(12) United States Patent
McGuckin, Jr.

(10) Patent No.: US 9,668,861 B2
(45) Date of Patent: Jun. 6, 2017

(54) VASCULAR DEVICE FOR TREATING VENOUS VALVE INSUFFICIENCY

(71) Applicant: Rex Medical, L.P., Conshohocken, PA (US)

(72) Inventor: James F. McGuckin, Jr., Radnor, PA (US)

(73) Assignee: Rex Medical, L.P., Conshohocken, PA (US)

( * ) Notice: Subject to any disclaimer, the term of this patent is extended or adjusted under 35 U.S.C. 154(b) by 163 days.

(21) Appl. No.: 14/616,675

(22) Filed: Feb. 7, 2015

(65) Prior Publication Data
US 2015/0257885 A1    Sep. 17, 2015

Related U.S. Application Data

(60) Provisional application No. 61/953,828, filed on Mar. 15, 2014.

(51) Int. Cl.
*A61F 2/06* (2013.01)
*A61F 2/24* (2006.01)

(52) U.S. Cl.
CPC .......... *A61F 2/2475* (2013.01); *A61F 2/2436* (2013.01); *A61F 2230/0067* (2013.01); *A61F 2230/0091* (2013.01); *A61F 2250/001* (2013.01)

(58) Field of Classification Search
CPC ........ A61F 2/88; A61F 2/2475; A61F 2/2412; A61F 2/2436; A61F 2250/001
See application file for complete search history.

(56) References Cited

U.S. PATENT DOCUMENTS

| | | |
|---|---|---|
| 4,275,469 A | 6/1981 | Gabbay |
| 4,759,758 A | 7/1988 | Gabbay |
| 5,019,102 A | 5/1991 | Hoene |
| 5,147,389 A | 9/1992 | Lane |
| 5,151,105 A | 9/1992 | Kwan-Gett |
| 5,258,022 A | 11/1993 | Davidson |
| 5,350,398 A | 9/1994 | Pavenik et al. |
| 5,358,518 A | 10/1994 | Camilli |

(Continued)

FOREIGN PATENT DOCUMENTS

| | | |
|---|---|---|
| EP | 1894543 | 3/2008 |
| WO | WO/9740755 | 11/1997 |

(Continued)

OTHER PUBLICATIONS

The Extended European Search Report from Application No. 15158728.4 dated Aug. 4, 2015.

*Primary Examiner* — Brian Dukert
(74) *Attorney, Agent, or Firm* — Neil D. Gershon

(57) ABSTRACT

A vascular device for treating vein valve insufficiency including an elongated member, a first retention portion movable from a first elongated insertion position to an expanded position and a second retention portion movable from a first elongated insertion position to an expanded position. An intermediate looped portion is positioned between the first portion and the second portion. The valve is supported by the intermediate looped portion and is movable between an open position to allow blood flow therethrough and a closed position to inhibit blood flow therethrough. The intermediate looped portion is adjustable to loops of different diameters dependent on an inner diameter of the vessel wall.

18 Claims, 10 Drawing Sheets

(56) References Cited

U.S. PATENT DOCUMENTS

| | | |
|---|---|---|
| 5,375,612 A | 12/1994 | Cottenceau et al. |
| 5,395,390 A | 3/1995 | Simon et al. |
| 5,397,351 A | 3/1995 | Pavcnik et al. |
| 5,397,355 A | 3/1995 | Marin |
| 5,411,552 A | 5/1995 | Andersen |
| 5,443,500 A | 8/1995 | Sigwart |
| 5,500,014 A | 3/1996 | Quijano et al. |
| 5,540,712 A | 7/1996 | Kleshinski et al. |
| 5,545,210 A | 8/1996 | Hess et al. |
| 5,562,728 A | 10/1996 | Lazarus |
| 5,591,197 A | 1/1997 | Orth |
| 5,593,417 A | 1/1997 | Rhodes |
| 5,609,598 A | 3/1997 | Laufer |
| 5,643,278 A | 7/1997 | Wijay |
| 5,674,279 A | 10/1997 | Wright |
| 5,746,766 A | 5/1998 | Edoga |
| 5,792,155 A | 8/1998 | Van Cleef |
| 5,800,526 A | 9/1998 | Anderson et al. |
| 5,810,847 A | 9/1998 | Laufer et al. |
| 5,827,322 A | 10/1998 | Williams |
| 5,843,164 A | 12/1998 | Frantzen et al. |
| 5,855,601 A | 1/1999 | Bessler et al. |
| 5,876,434 A | 3/1999 | Flomenblit et al. |
| 5,885,258 A | 3/1999 | Sachdeva et al. |
| 5,902,317 A | 5/1999 | Kleshinski et al. |
| 5,957,949 A | 9/1999 | Leonhardt et al. |
| 6,004,347 A | 12/1999 | McNamara et al. |
| 6,004,348 A | 12/1999 | Banas et al. |
| 6,014,589 A | 1/2000 | Farley et al. |
| 6,027,525 A | 2/2000 | Suh et al. |
| 6,033,398 A | 3/2000 | Farley et al. |
| 6,036,687 A | 3/2000 | Laufer et al. |
| 6,042,606 A | 3/2000 | Frantzen |
| 6,053,896 A | 4/2000 | Wilson et al. |
| 6,071,277 A | 6/2000 | Farley et al. |
| 6,080,160 A | 6/2000 | Chen et al. |
| 6,086,610 A | 7/2000 | Duerig et al. |
| 6,113,612 A | 9/2000 | Swanson et al. |
| 6,120,534 A | 9/2000 | Ruiz |
| 6,129,758 A | 10/2000 | Love |
| 6,136,025 A | 10/2000 | Barbut et al. |
| 6,139,536 A | 10/2000 | Mikus et al. |
| 6,149,660 A | 11/2000 | Laufer et al. |
| 6,162,245 A | 12/2000 | Jayaraman |
| 6,179,878 B1 | 1/2001 | Duerig et al. |
| 6,200,336 B1 | 3/2001 | Pavcnik et al. |
| 6,221,102 B1 | 4/2001 | Baker et al. |
| 6,224,626 B1 | 5/2001 | Steinke |
| 6,231,561 B1 | 5/2001 | Frazier et al. |
| 6,254,564 B1 | 7/2001 | Wik et al. |
| 6,258,118 B1 | 7/2001 | Baum et al. |
| 6,287,339 B1 | 9/2001 | Vasques et al. |
| 6,290,721 B1 | 9/2001 | Heath |
| 6,299,636 B1 | 10/2001 | Schmitt et al. |
| 6,299,637 B1 | 10/2001 | Shaolian et al. |
| 6,302,917 B1 | 10/2001 | Dua et al. |
| 6,309,416 B1 | 10/2001 | Swanson et al. |
| 6,425,915 B1 | 7/2002 | Khosravi et al. |
| 6,440,163 B1 | 8/2002 | Swanson et al. |
| 6,454,799 B1 | 9/2002 | Schreck |
| 6,503,272 B2 | 1/2003 | Duerig et al. |
| 6,511,491 B2 | 1/2003 | Grudem et al. |
| 6,527,800 B1 | 3/2003 | McGuckin et al. |
| 6,572,646 B1 | 6/2003 | Boylan et al. |
| 6,582,461 B1 | 6/2003 | Burmeister et al. |
| 6,626,899 B2 | 9/2003 | Houser et al. |
| 6,635,080 B1 | 10/2003 | Lauterjung et al. |
| 6,695,878 B2 | 2/2004 | McGuckin et al. |
| 6,733,525 B2 | 5/2004 | Yang et al. |
| 6,740,111 B1 | 5/2004 | Lauterjung |
| 7,007,698 B2 | 3/2006 | Thornton |
| 7,041,128 B2 | 5/2006 | McGuckin et al. |
| 8,109,990 B2 * | 2/2012 | Paul .............. A61F 2/2412 623/1.15 |
| 8,348,997 B2 * | 1/2013 | Thompson ........ A61F 2/2412 623/1.26 |
| 2001/0005787 A1 | 6/2001 | Oz et al. |
| 2001/0039432 A1 | 11/2001 | Whitcher et al. |
| 2002/0002401 A1 | 1/2002 | McGuckin et al. |
| 2002/0032481 A1 | 3/2002 | Gabbay |
| 2002/0055772 A1 | 5/2002 | McGuckin et al. |
| 2002/0138129 A1 | 9/2002 | Armstrong et al. |
| 2003/0018294 A1 | 1/2003 | Cox |
| 2003/0199987 A1 | 10/2003 | Berg et al. |
| 2004/0098098 A1 | 5/2004 | McGuckin, Jr. et al. |
| 2004/0220593 A1 | 11/2004 | Greenhalgh |
| 2005/0049692 A1 | 3/2005 | Numamoto et al. |
| 2006/0122692 A1 | 6/2006 | Gilad et al. |
| 2006/0149360 A1 | 7/2006 | Schwammenthal et al. |
| 2006/0190074 A1 | 8/2006 | Hill et al. |
| 2007/0112423 A1 | 5/2007 | Chu |
| 2007/0185571 A1 | 8/2007 | Kapadia et al. |
| 2008/0221669 A1 | 9/2008 | Camilli et al. |
| 2008/0294189 A1 | 11/2008 | Moll et al. |
| 2009/0062901 A1 | 3/2009 | McGuckin, Jr. |
| 2010/0030253 A1 | 2/2010 | Harris et al. |
| 2010/0217385 A1 | 8/2010 | Thompson et al. |
| 2011/0202127 A1 | 8/2011 | Mauch et al. |

FOREIGN PATENT DOCUMENTS

| | | |
|---|---|---|
| WO | WO/9819629 | 5/1998 |
| WO | WO/9956655 | 11/1999 |
| WO | WO/0128459 | 4/2001 |
| WO | 01/49213 | 7/2001 |
| WO | WO02/100297 | 12/2002 |
| WO | 2006/004679 | 1/2006 |
| WO | WO2007/067942 | 6/2007 |
| WO | WO2008/100382 | 8/2008 |

* cited by examiner

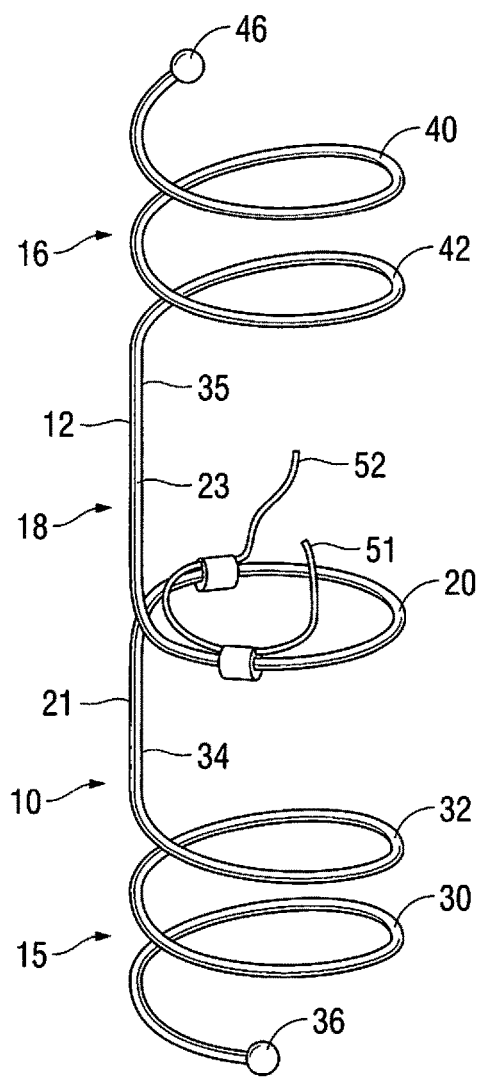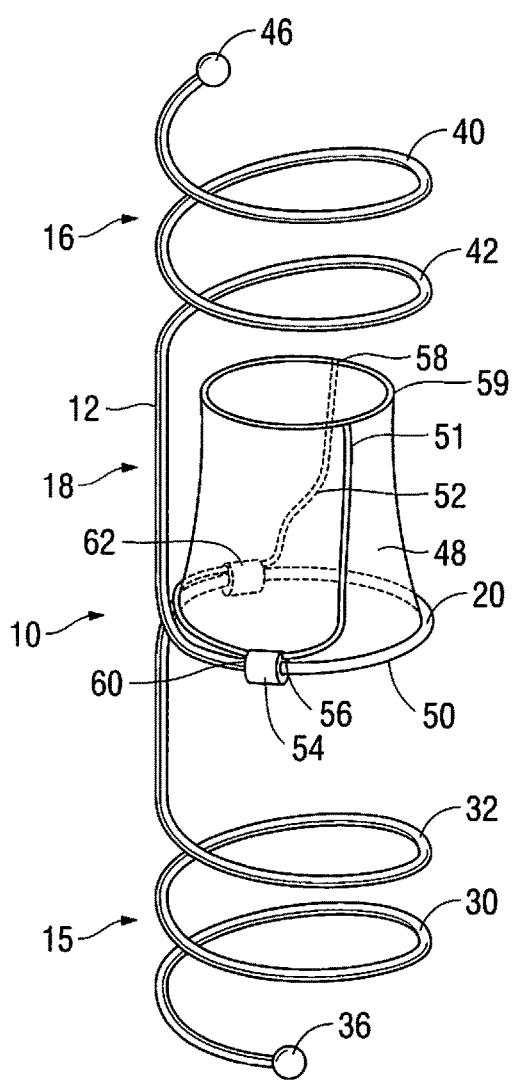

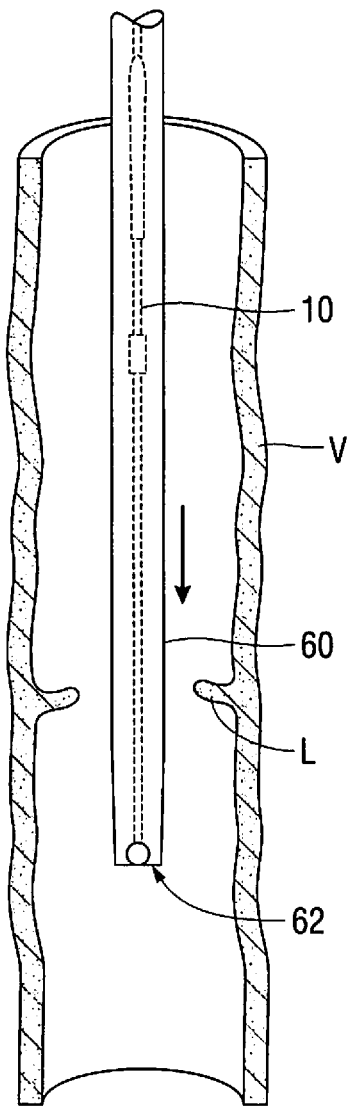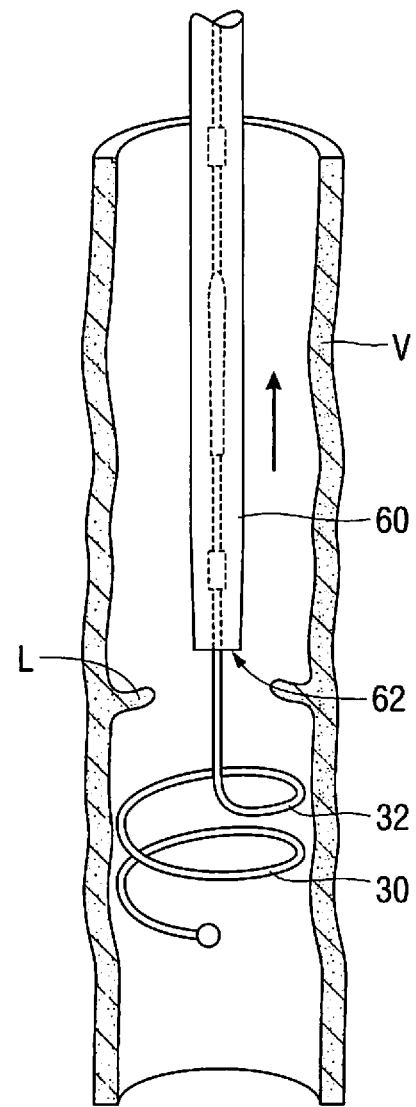
FIG. 7A　　　　FIG. 7B

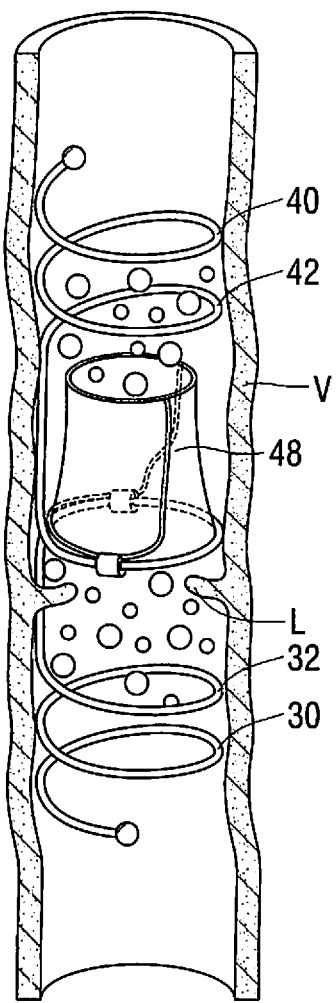
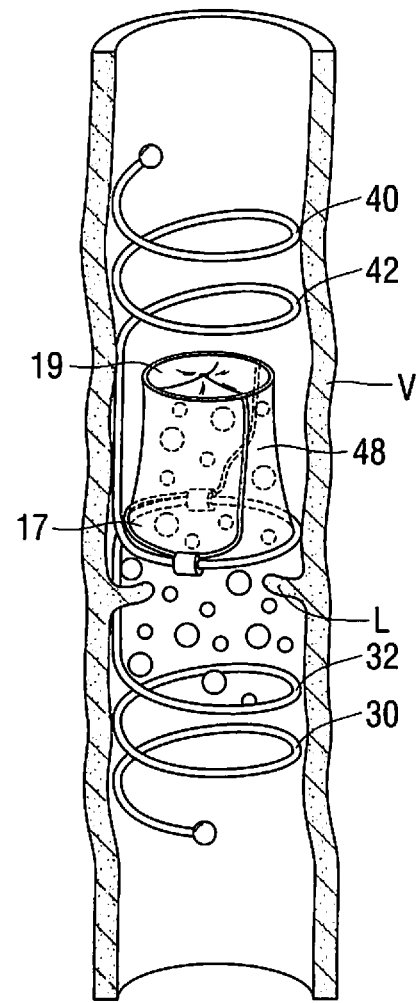
FIG. 7E  FIG. 7F

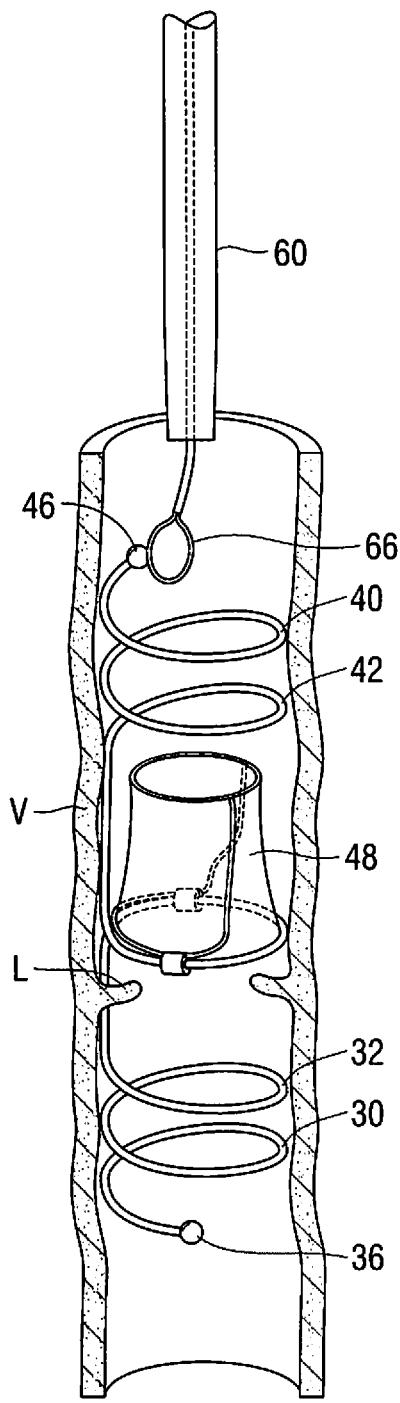 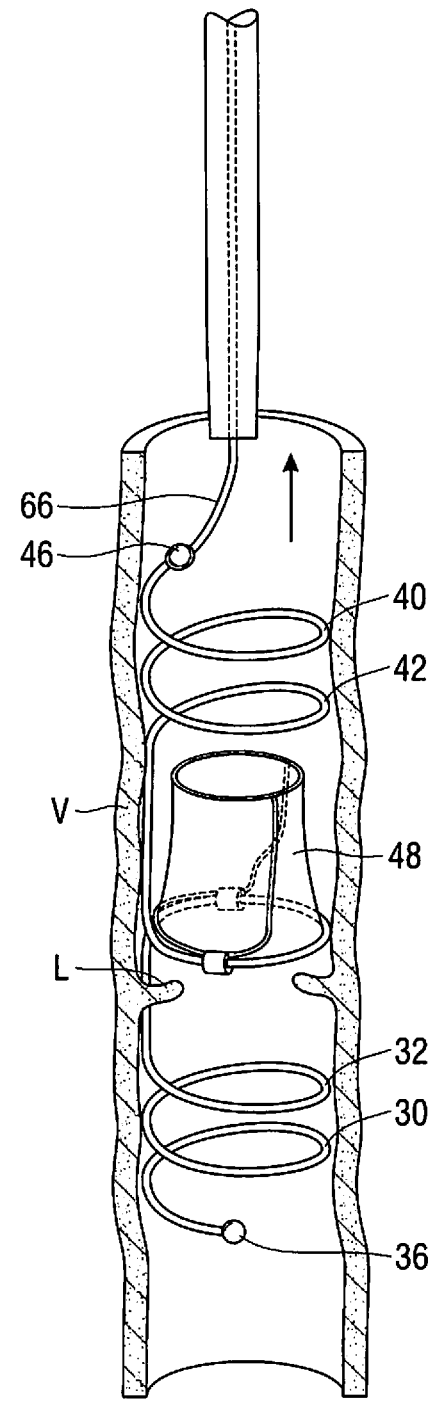
FIG. 7G  FIG. 7H

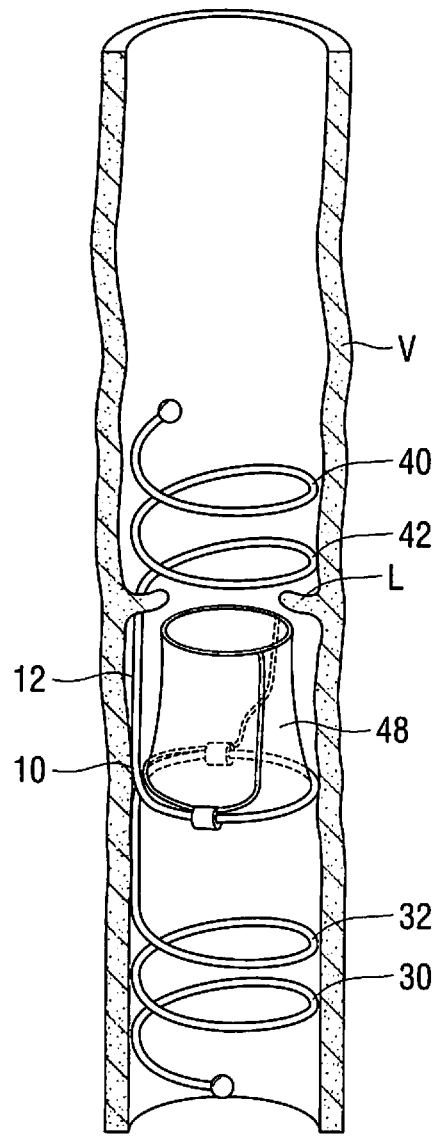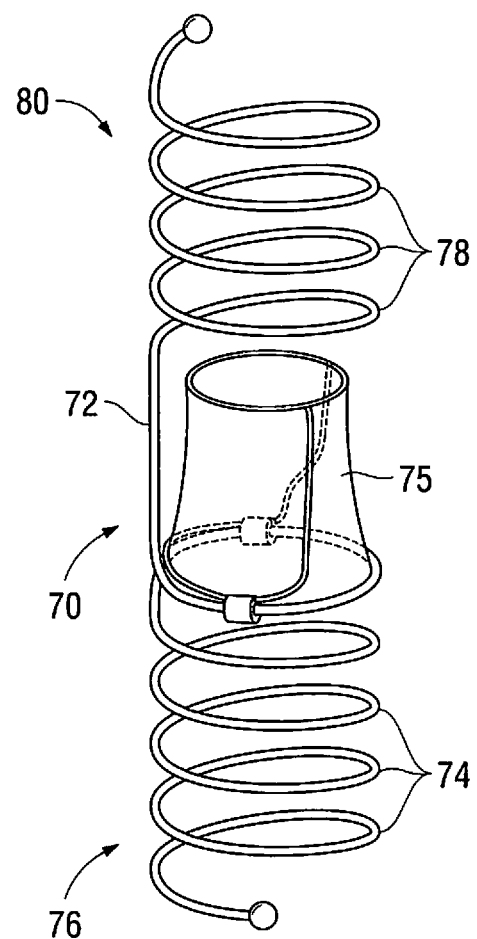
FIG. 8
FIG. 9

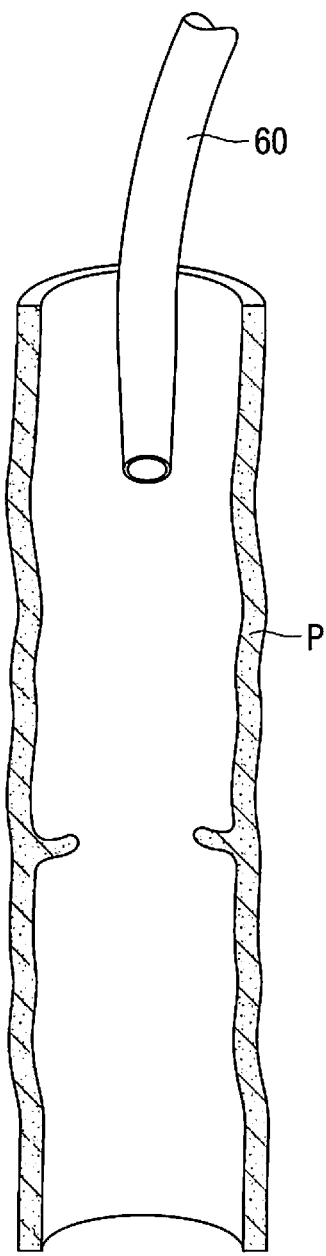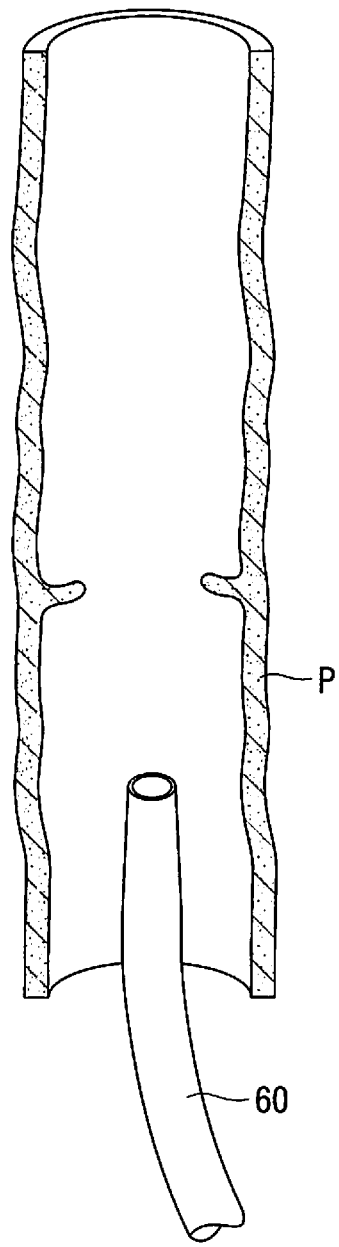
FIG. 13A
FIG. 13B

VASCULAR DEVICE FOR TREATING VENOUS VALVE INSUFFICIENCY

This application claims priority from provisional application Ser. No. 61/953,828, filed Mar. 15, 2014, the entire contents of which are incorporated herein by reference.

BACKGROUND

Technical Field

This application relates to a vascular device and more particularly to a vascular device with a valve for treating venous valve insufficiency.

Background of Related Art

Veins in the body transport blood to the heart and arteries carry blood away from the heart. The veins have one-way valve structures in the form of leaflets disposed annularly along the inside wall of the vein which open to permit blood flow toward the heart and close to prevent back flow. That is, when blood flows through the vein, the pressure forces the valve leaflets apart as they flex in the direction of blood flow and move towards the inside wall of the vessel, creating an opening therebetween for blood flow. The leaflets, however, do not normally bend in the opposite direction and therefore return to a closed position to prevent blood flow in the opposite, i.e. retrograde, direction after the pressure is relieved. The leaflet structures, when functioning properly, extend radially inwardly toward one another such that the tips contact each other to block backflow of blood.

In the condition of venous valve insufficiency, the valve leaflets do not function properly as they thicken and lose flexibility, resulting in their inability to extend sufficiently radially inwardly to enable their tips to come into sufficient contact with each other to prevent retrograde blood flow. The retrograde blood flow causes the buildup of hydrostatic pressure on the residual valves and the weight of the blood dilates the wall of the vessel. Such retrograde blood flow, commonly referred to as reflux, leads to swelling and varicose veins, causing great discomfort and pain to the patient. Such retrograde blood flow, if left untreated can also cause venous stasis ulcers of the skin and subcutaneous tissue. There are generally two types of venous valve insufficiency: primary and secondary. Primary venous valve insufficiency is typically a condition from birth, where the vein is simply too large in relation to the leaflets so that the leaflets cannot come into adequate contact to prevent backflow. More common is secondary venous valve insufficiency which is caused by clots which gel and scar, thereby changing the configuration of the leaflets, i.e., thickening the leaflets creating a "stub-like" configuration. Venous valve insufficiency can occur in the superficial venous system, such as the saphenous veins in the leg, or in the deep venous system, such as the femoral and popliteal veins extending along the back of the knee to the groin.

A common method of treatment of venous valve insufficiency is placement of an elastic stocking around the patient's leg to apply external pressure to the vein, forcing the walls radially inwardly to force the leaflets into apposition. Although sometimes successful, the tight stocking is quite uncomfortable, especially in warm weather, as the stocking must be constantly worn to keep the leaflets in apposition. The elastic stocking also affects the patient's physical appearance, thereby potentially having an adverse psychological affect. This physical and/or psychological discomfort sometimes results in the patient remove the stocking, thereby preventing adequate treatment.

Another method of treatment has been developed to avoid the discomfort of the stocking. This method involves major surgery requiring the implantation of a cuff internally of the body, directly around the vein. This surgery requires a large incision, resulting in a long patient recovery time, scarring and carries the risks, e.g., anesthesia, inherent with surgery.

Another invasive method of surgery involves selective repairing of the valve leaflets, referred to as valvuloplasty. In one method, sutures are utilized to bring the free edges of the valve cusp into contact. This procedure is complicated and has the same disadvantages of the major surgery described above.

Commonly assigned U.S. Pat. Nos. 6,695,878 and 6,527,800, the entire contents of which are incorporated herein by reference, disclose a method and device to minimally invasively treat venous valve insufficiency without requiring an outer stocking or internal cuff. Such device avoids the physical and psychological discomfort of an external stocking as well as avoids the risk, complexity and expense of surgically implanted cuffs. The device is advantageously inserted minimally invasively, i.e., intravascularly, and functions to effectively bring the valve leaflets into apposition. This device first expands against the vessel wall to grasp the wall, and then contracts to bring the vessel wall radially inwardly so the leaflets can be pulled closer together to a functional position.

The vascular device of commonly assigned U.S. Pat. No. 6,676,698, the entire contents of which are incorporated herein by reference, utilizes the device of these foregoing U.S. Pat. Nos. 6,695,878 and 6,527,800 for bringing the vessel wall radially inwardly to correct the dilation of the wall, but rather than rely on the patient's existing valve leaflets which may be scarred or non-functional, contains a replacement valve as a substitute for the patient's leaflets. Thus, advantageously, venous valve insufficiency can be treated minimally invasively by bringing the vessel wall inwardly and replacing the patient's valve.

Commonly assigned U.S. Pat. No. 8,834,551 discloses another device for bringing the vessel wall radially inwardly for treating venous valve insufficiency having retention arms extending to a distal end of the valve. Commonly assigned U.S. Publication No. 2013-0289710 discloses another vascular device wherein release of the retention members causes the struts to pull the vessel wall inwardly.

Although the foregoing devices have certain advantages in approximating the vessel wall, in certain applications such approximation might be difficult or not achieve sufficient approximation as vessel wall diameters vary. There exists a need for a device for treating venous valve insufficiency which relies on the existing vessel wall spacing but is adjustable to different size vessels and provides a replacement valve. Such adjustability would advantageously enable the use of a single device for different size vessels for implantation of a valve to replace and simulate the patient's valve.

SUMMARY OF THE INVENTION

The present application provides in one aspect a vascular device comprising a body having a proximal portion and a distal portion and movable from a collapsed elongated insertion position to an expanded position having a larger cross-sectional dimension. The body includes a proximal looped portion, a distal looped portion and an intermediate valve-supporting looped portion. The intermediate looped portion supports a valve, wherein the valve is movable between an open position to allow blood flow and a closed position to inhibit blood flow. The intermediate looped portion is adjustable to different loop diameters depending on a size of the vessel in which it is inserted.

In accordance with another aspect, the present invention provides a vascular device for treating vein valve insufficiency comprising an elongated member having a first upstream portion and a second downstream portion. A first retention portion at the upstream portion is movable from a first elongated insertion position to an expanded position, and a second retention portion at the downstream portion is movable from a first elongated insertion position to an expanded position. An intermediate looped portion is positioned between the first portion and the second portion. A valve is supported by the intermediate looped portion and is movable between an open position to allow blood flow therethrough and a closed position to inhibit blood flow therethrough. The intermediate looped portion is adjustable to loops of different diameters dependent on an inner diameter of the vessel wall.

In some embodiments, the first retention portion is a looped portion and/or the second retention portion is a looped portion. In some embodiments, the first retention portion includes first and second looped portions and/or the second retention portion includes first and second looped portions. In some embodiments, the first and second retention portions are substantially perpendicular to a longitudinal axis of the elongated member. In some embodiments, the first and second retention portions extend on only one side of the elongated member.

In some embodiments, a collar is mounted on the intermediate looped portion. In some embodiments, first and second members extend from the intermediate looped portion to retain the valve. In some embodiments, the second member is slidable with respect to the intermediate looped portion and in some embodiments is attached to a first collar mounted on the intermediate looped portion and slidable within a second collar. In some embodiments, the first member is fixedly attached to the intermediate looped portion.

In some embodiments, the elongated member, the intermediate looped portion, the first retention portion and the second retention portion are formed from a single wire.

The valve can in some embodiments have a substantially conical configuration.

The device can include a retrieval structure at the upstream and/or downstream portions of the elongated member for retrieval of the device.

In accordance with another aspect, the present invention provides a method for treating venous valve insufficiency comprising:

providing a vascular device including an elongated portion, downstream, upstream and intermediate looped portions extending radially from the elongated portion, and a valve attached to the intermediate looped portion;

inserting into a target vessel a delivery device and the vascular device in an insertion position within the delivery device, wherein in the insertion position the downstream, upstream and intermediate looped portions have a reduced transverse dimension; and exposing the vascular device from the delivery device, wherein exposing the vascular device enables the downstream, upstream and intermediate looped portions to move to expanded positions, the intermediate looped portion engaging an internal wall of the vessel and automatically adjusting to a diameter of the vessel.

In some embodiments, the diameter of the valve is adjusted by a radial support attached to the valve and slidably connected to the intermediate looped portion. In some embodiments, a collar is mounted to the intermediate looped portion, and the radial support is slidable within the collar.

BRIEF DESCRIPTION OF THE DRAWINGS

Preferred embodiment(s) of the present disclosure are described herein with reference to the drawings wherein:

FIG. 1 is a perspective view of a first embodiment of the vascular device of the present invention shown with the replacement valve removed for clarity;

FIG. 2 is a perspective view of the vascular device of FIG. 1 shown with the replacement valve;

FIG. 7A illustrates a delivery tube being inserted retrograde inside the vessel, upstream of the patient's valve leaflets, for delivery of the vascular device of FIG. 2;

FIG. 7B is a view similar to FIG. 7A showing withdrawal of the delivery tube to partially expose the vascular device of FIG. 2;

FIG. 7E is a view similar to FIG. 7D showing the valve in an open position to enable blood flow therethrough;

FIG. 7F is a view similar to FIG. 7E showing the valve in the closed position to prevent blood flow therethrough;

FIGS. 7G and 7H are views similar to FIG. 7F showing introduction of a retrieval device to engage the retrieval structure of the vascular device for retrieval from the vessel;

FIG. 8 illustrates placement of the vascular device of FIG. 2 upstream of the patient's valve leaflets;

FIG. 9 illustrates an alternate embodiment of the vascular device of the present invention;

FIG. 13A shows a side view of the delivery device for the vascular device of FIG. 2, with the vessel wall shown in section, illustrating retrograde insertion of the delivery device in the popliteal vein; and FIG. 13B shows a side view of the delivery device for the vascular device of FIG. 2, with the vessel wall shown in section, illustrating antegrade insertion of the delivery device in the popliteal vein;

DETAILED DESCRIPTION OF PREFERRED EMBODIMENTS

Figure 3:
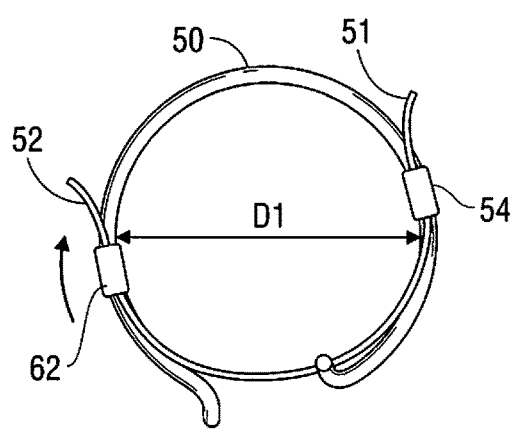
FIG. 3 is top view of the intermediate portion of the valve support of the vascular device of FIG. 1 shown in a first position to define a first gap.

Referring now in detail to the drawings where like reference numerals identify similar or like components throughout the several views, the device is designated generally by reference numeral 10 and has an elongated insertion position for minimally invasive insertion and an expanded position when placed inside the vessel to provide a valve to replace the patient's valve. The vascular device 10 can be used to replace the patient's valve leaflets after the valve leaflets are removed or placed upstream or downstream of the existing non-functioning valve leaflets of the patient without having to surgically remove the valve leaflets.

FIGS. 1 and 2 illustrate vascular device 10 of a first embodiment of the present invention in the expanded configuration, with FIG. 1 shown without the replacement valve attached for clarity.

Vascular device 10 includes a valve support 12 and a replacement valve 48. Valve support 12 is preferably composed of a shape memory material, such as a nickel-titanium alloy, e.g. Nitinol, so that in its memorized configuration it assumes the shape shown in FIGS. 1 and 2. This shape memory material characteristically exhibits rigidity in the austenitic state and more flexibility in the martensitic state.

In some embodiments, to facilitate passage from the delivery catheter, the shape memory device is maintained in a collapsed configuration inside a delivery sheath or delivery catheter where it is cooled by a saline solution to maintain the device below its transition temperature. The cold saline maintains the temperature dependent device in a relatively softer condition as it is in the martensitic state within the delivery sheath. This facilitates the exit of valve support 12 from the sheath as frictional contact between the device and the inner wall of the sheath would otherwise occur if the device was maintained in a rigid, i.e. austenitic, condition. When the valve support 12 is released from the sheath to the target site, it is warmed by body temperature, thereby transitioning in response to this change in temperature to an austenitic expanded condition. In other embodiments, the valve support is maintained in a martensitic state within the delivery sheath (catheter) and then returns to its shape memorized austenitic when exposed from the delivery tube.

The valve support 12 has an upstream portion 15, a downstream portion 16 and an intermediate portion 18 positioned between the downstream portion 16 and upstream portion 15. FIG. 7A illustrates the device 10 in the collapsed position within a delivery tube (catheter) or sheath 60, the collapsed position enabling minimally invasive insertion of the device 10 to the target vessel. As shown, in the collapsed reduced profile position the device is elongated, substantially aligned with a longitudinal axis of the delivery sheath 60, and when exposed through the distal opening 62 of the sheath 60, it moves to its expanded position.

As used herein, antegrade, as is known in the art, denotes in the direction of blood flow and retrograde denotes in a direction against the direction of blood flow. Upstream and downstream as is conventional are used herein to correlate to the direction of blood flow which flows upstream to downstream.

The valve support 12 of device 10 is preferably formed from shape memory wires. The first main wire 20 provides the retention for the device 10 within the vessel. It also provides support for the replacement valve 48. The second and third wires 51, 52, respectively, help to support the replacement valve 48 and provide for adjustability of the valve as described in more detail below.

In the expanded condition (configuration), at the upstream portion 15, at least one wire loop is formed, and in the illustrated embodiment two wire loops 30, 32 are formed. The wire loops or rings 30, 32 extend radially from the elongated portion 34 of wire 20 and preferably extend on only one side of wire 20 as shown. Stated another wire, wire 20 has an elongated portion 34 extending longitudinally within the vessel, and loops 30, 32 extend in one direction with respect to the longitudinal axis of the elongated portion 34. The loops 30, 32 are shown substantially perpendicular to the longitudinal axis of the elongated portion 34 so that they circumferentially engage the circumference of the vessel wall and openings through the loops 30, 32 enable blood flow therethrough. That is, a line passing through the center of the loops 30, 32 would be substantially parallel to the longitudinal axis of the elongated portion 34. Alternatively, the loops 30, 32 can be at acute angles with respect to the longitudinal axis of elongated portion 34.

In the expanded condition (configuration), at the downstream portion 16, at least one wire loop is formed, and in the illustrated embodiment two wire loops 40, 42 are formed. The wire loops or rings 40, 42 extend radially from the elongated wire 20, and preferably extend on only one side of wire 20 as shown. That is, the wire loops 40 and 42 preferably extend to the same side of elongated wire portion 35, and on the same side as wire loops 30, 32. The loops 40, 42 are shown substantially perpendicular to the longitudinal axis of the elongated portion 35 so that they circumferentially engage the circumference of the vessel wall and openings through the loops 40, 42 enable blood flow therethrough. That is, a line passing through the center of the loops 40, 42 would be substantially parallel to the longitudinal axis of the elongated portion 35 and would also pass through the center of the loops 30, 32. Alternatively, the loops 40, 42 can be at acute angles with respect to the longitudinal axis of elongated portion 35.

In a preferred embodiment, the elongated wire is a monolithic wire so that the loops 30, 32, 40 and 42 are monolithically formed with the wire 20. However, it should be appreciated in alternate embodiments, separate wires attached, e.g., welded, can be utilized to form the valve support 12.

Also, although two wire loops are shown at the upstream portion 15 and downstream portion 16, a different number of wire loops can be placed at the downstream or upstream portion. For example, in the embodiment of FIG. 9, vascular device 70 has a valve support 72 which includes a plurality of spiral wire loops, with multiple wire loops 74 at the upstream portion 76 and multiple wire loops 78 at downstream portion 80. In all other respects, valve support 72 and replacement valve 75 are identical to valve support 12 and valve 14 of FIG. 2 and therefore for brevity are not discussed in further detail since the structure and function is the same as in FIG. 2 and the insertion methods are the same as described and illustrated herein.

Retrieval structure 36 is positioned on or adjacent an upstream tip of the main wire 20. Similarly, as an alternative or in addition to retrieval structure 36, retrieval structure 46 is positioned on or adjacent a downstream tip of the main wire 20. The retrieval structure 36, 46 can include a ball, a hook or other structure which can be grasped by a removal tool, such as snare or grasper, to remove the device 10. By providing retrieval structure on both sides of the device 10 in certain embodiments, the device 10 can advantageously be removed in either an antegrade or retrograde direction.

The intermediate portion 18 of valve support 12 includes a valve mounting section to function as the support for the valve 48. As shown in FIG. 1, the wire 20 loops a full 360 degrees to form a supporting loop 50. Attached to the supporting loop or ring 50 are wires 51 and 52. Wires 51 and 52 are also preferably made of shape memory material and in the collapsed delivery position (condition) extend longitudinally along the wire 30. A first end 59 of wire 51 is fixedly attached to an upper portion of valve 48 and a second opposite end 56 is fixedly attached to collar 54. Thus, wire 51 helps to secure valve 48 to valve support 12. Wire 52 has a first end 58 fixedly attached to an upper portion of the valve 48 and a second opposite end 60 which extends through collar 62 and is attached to collar 54. Wire 52 slides within collar 62 as the diameter of the supporting loop 50 changes to conform to the diameter of the vessel in which it is placed to thereby adjust the diameter of the valve 48. That is, when the vascular device 10 is placed in a vessel, the diameter of the supporting loop 50 can change, e.g., be reduced in diameter and the wire 52 can slide to pull the valve 48 to a smaller diameter position. This helps to maintain the desired configuration of the valve 48. In this manner of adjustment of the supporting loop 50 and the valve 48, the vascular device 10 can be used in different sized vessels.

Figure 4:
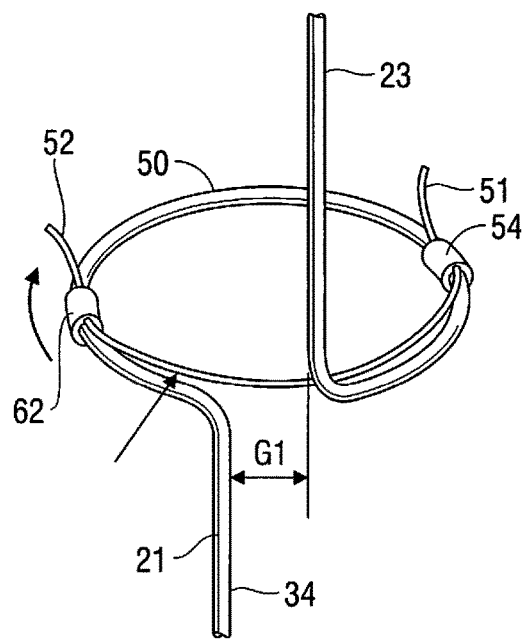
FIG. 4 is a perspective view of the intermediate portion of the valve support of the vascular device of FIG. 1 shown with the gap of FIG. 3.
Figure 5:
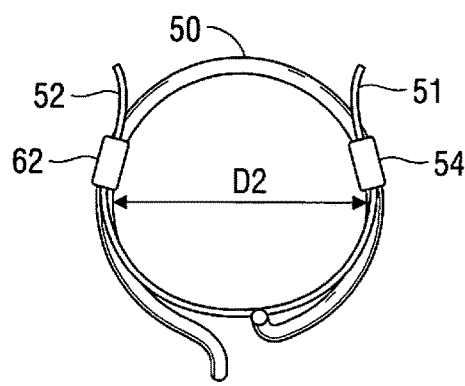
FIG. 5 is a top view similar to FIG. 3 showing a second smaller gap when the vascular device is placed in a smaller diameter vessel.
Figure 6:
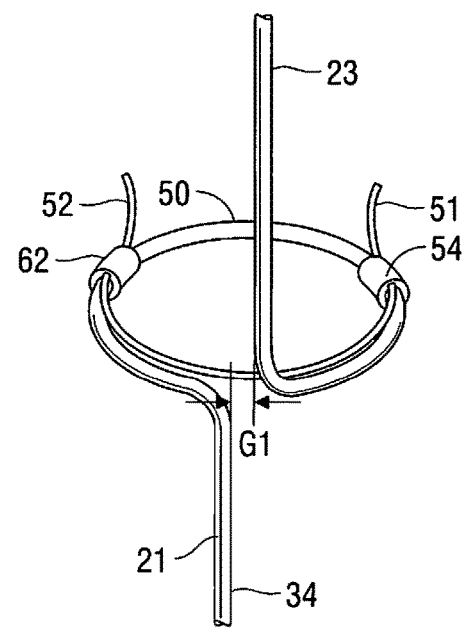
FIG. 6 is a perspective view of the intermediate portion of the valve support of the vascular device of FIG. 1 shown with the gap of FIG. 5.

This adjustability can be appreciated by comparing FIGS. 3-6. In FIGS. 3 and 4, the supporting loop 50 of wire 20 has a first diameter D1 which forms a gap G1 between the opposite directed portions 21, 23 of the elongate wire 20. FIGS. 5 and 6 illustrate what occurs if the vascular device 10 is placed in a smaller vessel. As shown, the supporting loop 50 of wire 20 is moved inwardly to define a diameter D2 which is smaller than the diameter D1 of FIG. 3. Likewise, the gap G2 formed between the portions 21, 23 of elongate wire 20 is less than the gap G1 of FIG. 4. The change in the valve dimension due to the sliding movement of wire 52 can be appreciated by comparing FIGS. 7C and 7D. If placed in smaller sized vessel, the supporting loop 50 is moved to smaller diameter in the direction of the arrow of FIG. 7C and the wire 52 slides within the collar 62 to pull the valve 48 to a smaller diameter as shown in FIG. 7D.

The wires or struts 51, 52 can extend longitudinally along and external to the valve 48 and then bend inwardly at an angle, for example an angle of about 90 degrees but other angles are also contemplated, to form a radial portion extending substantially transversely to the longitudinal axis of the valve 48 to attach the valve 48. The valve 48 in some embodiments can include two spaced apart openings to accommodate passage of the radial portion of the wires 51, 52 to secure the valve to the struts or wires 51, 52. This engagement fixes the wires to the valve 48, enabling the valve 48 to move between open and closed positions while still being retained. In other embodiments, the wires 51, 52, do not have a radial portion and are attached to the valve at their downstream ends and/or along a portion or entire portion of the length of wires 51, 52.

Various types of valves can be utilized. In the illustrated embodiment, valve 48 is a substantially conically shaped valve with a base 17 attached to the supporting loop 50 and has slit valve 19 at its downstream end. In this manner, the slit valve 19 is closed (FIG. 7F) until the force of blood flow opens the valve to allow blood flow therethrough as shown in FIG. 7E. Other types of valves are also contemplated, including for example duckbill valves or valves disclosed in U.S. Pat. No. 6,676,698, incorporated herein by reference in its entirety. For example, the valve can have a plurality of leaflets or petals arranged circumferentially thereabout. The leaflets can fold inwardly towards each other in the closed position to prevent blood flow. The pressure of the blood during systole can force the leaflets apart to the open position. The valve opening can optionally be offset from the central longitudinal axis of the vascular device.

There are several different methods of insertion of the vascular devices of the present invention for treating venous valve insufficiency of the popliteal or saphenous vein. Such methods of insertion that can be utilized include the methods disclosed in detail in the U.S. Pat. No. 6,676,698 patent, which shows for example placement into the popliteal vein in the patient's leg and advanced to a region adjacent the leaflets to deploy the vascular device upstream of the leaflets. The delivery catheter is explained as delivered in an antegrade fashion, with the tip extending downstream of the leaflets to deploy the device just upstream (defined in reference to the direction of blood flow) of the leaflets.

Figure 10:
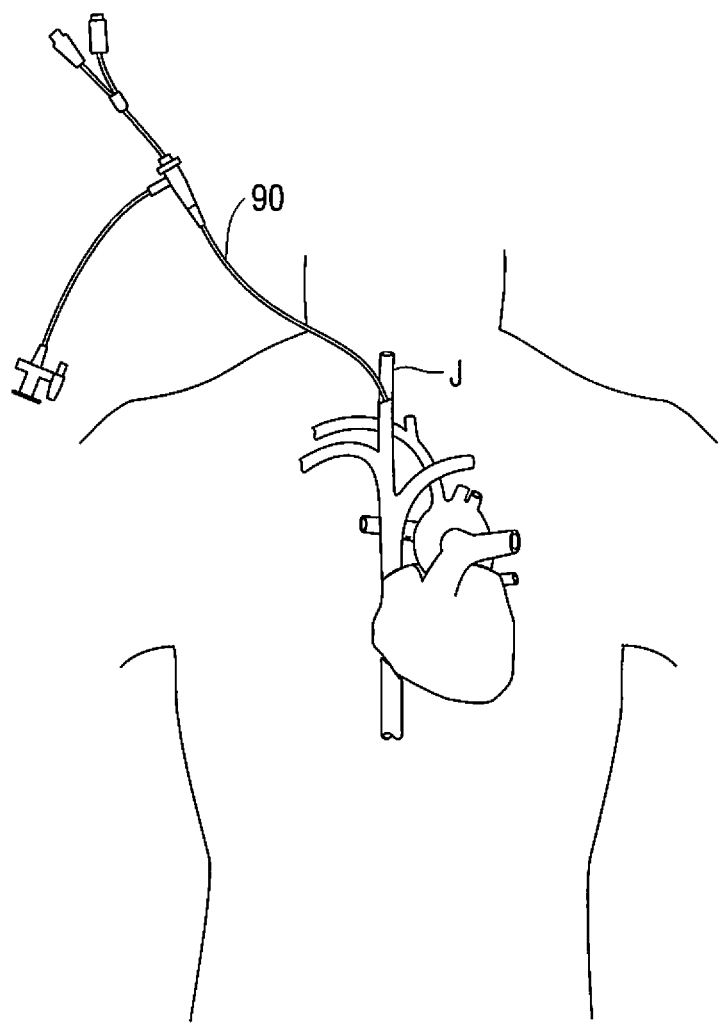
FIG. 10 illustrates one method of insertion of the vascular device of the present invention showing the delivery catheter inserted through the jugular vein for retrograde insertion into the popliteal vein.
Figure 11:
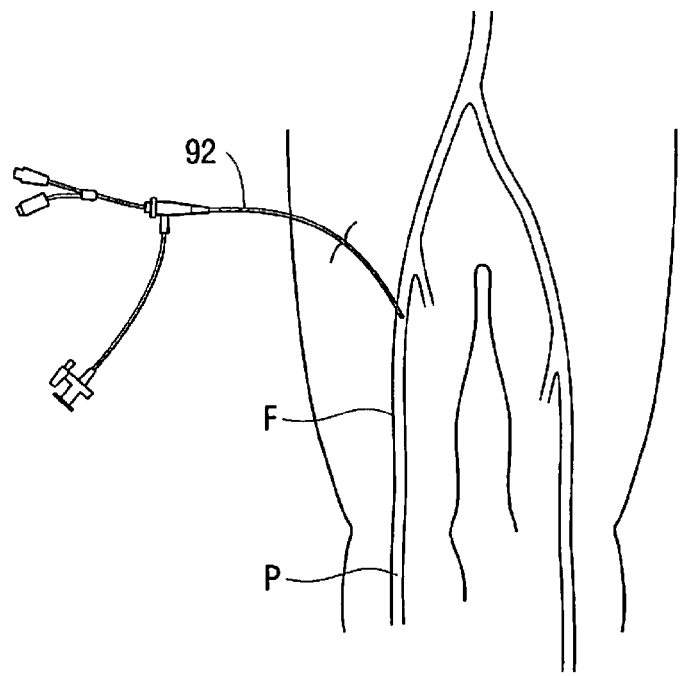
FIG. 11 illustrates another method of insertion of the vascular device of the present invention showing the delivery catheter inserted through the right femoral vein for retrograde access to the popliteal vein.
Figure 12:
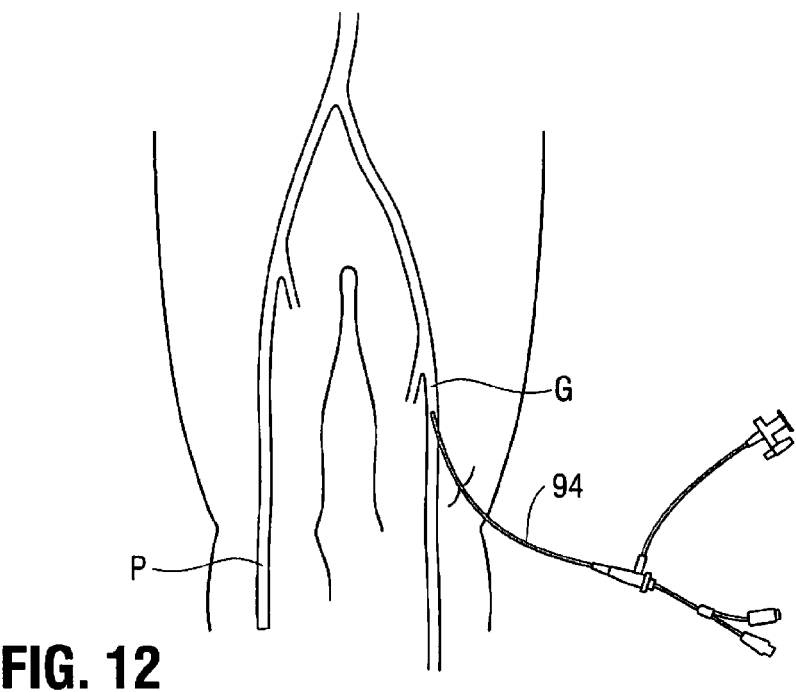
FIG. 12 illustrates yet another method of insertion of the vascular device of the present invention showing a contralateral approach wherein the delivery catheter is inserted through the left femoral vein for advancement around the iliac vein for retrograde insertion into the right popliteal vein.

The vascular devices of the present invention can be inserted through the right jugular vein J (FIG. 10) through delivery sheath 90, where the device will be advanced through the superior and inferior vena cava, past the iliac vein, through the femoral vein and into the popliteal vein through leaflets in a retrograde fashion, i.e., opposite the direction of blood flow. The delivery catheter can thus extend through the leaflet region just upstream of the leaflets or alternatively, just downstream of the leaflets. The vascular devices of the present invention can alternatively be placed in the right femoral vein F (FIG. 11) through delivery sheath 92, where it will be advanced in a retrograde manner to the popliteal vein P. In the contralateral approach, it is inserted through the left femoral vein G (FIG. 12) through delivery sheath 94 where it will be advanced around the iliac vein and through the left femoral vein into the popliteal vein P.

In use, in one method, the catheter or delivery sheath is inserted over a conventional guidewire (not shown) so the distal tip of the sheath extends past, i.e., upstream, of the valve leaflets L extending annularly from vessel wall of vessel V (FIG. 7A). As can be appreciated, since there is a gap between the valve leaflets, the valve cannot function properly because the leaflets cannot properly close to prevent backflow. Also, due to the malfunctioning of the valve, the vessel wall can become dilated as the weight and pressure of the backflow blood pushes out the vessel wall.

Figure 7C:
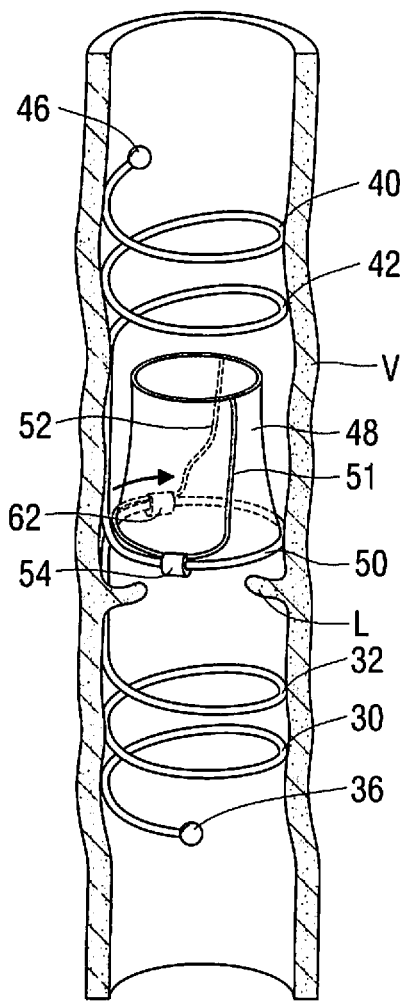
FIG. 7C shows full withdrawal of the delivery tube and full deployment of the vascular device of FIG. 2 downstream of the patient's valve leaflets.
Figure 7D:
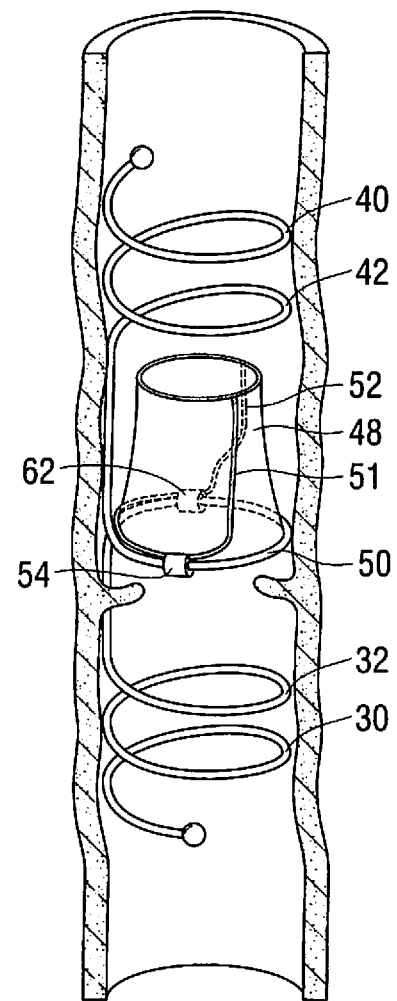
FIG. 7D is a view similar to FIG. 7C showing the vascular device moving to a smaller diameter due to the walls of the vessel.

Once the position of the sheath 60 is confirmed by venography, intravascular ultrasound, or other means, the sheath 60 is withdrawn with respect to the device 10 (FIG. 7B) to expose the device 10 so the support 12 returns to the memorized expanded configuration of FIG. 7C. To expose the device 10, a pusher can be advanced distally within delivery sheath 60 against the end of the device 10, or the delivery sheath 60 can be withdrawn, or both the pusher and delivery sheath are moved relative to each other. Note that device 70 can be inserted in the same way as device 10 and therefore reference to insertion of device 10 also contemplates inserting device 70.

The device is expanded to a larger diameter than the vessel diameter so that loops 30, 32, 40, 42 will engage the vessel wall to apply a sufficient radial force to secure the device 10 within the vessel. The replacement valve 48 remains inside the vessel and opens and closes to respectively enable and block blood flow therethrough. The valve support 12 e.g., intermediate support loop 50 and valve 48, can then adjust to the diameter of the vessel. In FIGS. 7C and 7E, the device 10 is placed upstream of the patient's valve leaflets L.

The vascular device 10 (and 70) can also be placed upstream (with respect to the direction of blood flow) of the valve leaflets. The delivery catheter can be inserted in the same retrograde manner as described above, except it is advanced adjacent but not past the valve leaflets L to enable downstream delivery of the device 10 (70) in an upstream position. The replacement valve 48 (75) would be placed upstream of the valve leaflets if left in the patient) or upstream of the region of the vessel where the valve leaflets were before removal. Thus, the replacement valve of the present invention can be utilized as a total replacement wherein the patient's valve leaflets are removed (such as in FIGS. 13A and 13B) or can be placed upstream or downstream of the patient's leaflets, leaving the nonfunctioning leaflets in place (such as in FIGS. 7C-7H). FIG. 13A shows the delivery device 60 inserted retrograde in the popliteal vein; FIG. 13B shows the delivery device 60 inserted antegrade in the popliteal vein.

The vascular device 10 is configured to minimize the insertion profile. To achieve this, the components of the device are aligned along a longitudinal axis during delivery.

As an alternative to shape memory, a stainless steel or polymeric vascular support could be utilized.

Valve 40 is conically shaped as shown and is secured to the wire 20 of the vascular device 10 by various techniques. Other types of valves can be utilized such as those described in the U.S. Pat. No. 6,676,698 patent.

As described above, the vascular device can be placed in the popliteal vein, the femoral vein or other veins. Placement of two or more vascular devices in the vein is also contemplated.

If it is desired to reposition or remove the device 10 (70), snare 66 can be inserted within delivery catheter 60 or another introducer sheath. The snare 66 is tightened around the retrieval structure 46 of vascular device 10, as shown in FIG. 7H. Alternatively, a snare can be inserted from the other direction and tightened on retrieval structure 36 to enable repositioning or removal of the device 10.

The foregoing valves can be attached to the vascular devices by sewing, molding or other techniques. The valves can be composed of a variety of materials such as PET, PTFE, polycarbonate polyurethane, swine intestinal submucosa, collagen and other biomaterials. The valve and/or the vascular device surface can optionally be coated with anti-platelet or anti-thrombin/anti-clotting materials, 2*b*/2*a* coating, receptors, heparin coating, endothelial cell coating, etc.

While the above description contains many specifics, those specifics should not be construed, as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A vascular device for treating vein valve insufficiency comprising:
   an elongated member having a first upstream portion and a second downstream portion;
   a first retention portion at the first upstream portion, the first retention portion movable from a first elongated insertion position to an expanded position;
   a second retention portion at the second downstream portion, the second retention portion movable from a first elongated insertion position to an expanded position:
   an intermediate looped portion positioned between the first upstream portion and the second downstream portion;
   a valve supported by the intermediate looped portion and movable between an open position to allow blood flow therethrough and a closed position to inhibit blood flow therethrough; and
   first and second members extending from the intermediate looped portion to retain the valve;
   wherein the intermediate looped portion is composed of a material enabling the intermediate looped portion to be adjustable to loops of different diameters dependent on an inner diameter of the vessel wall.

2. The vascular device of claim 1, wherein the first retention portion is a looped portion.

3. The vascular device of claim 2, wherein the second retention portion is a looped portion.

4. The vascular device of claim 1, wherein the second retention portion is a looped portion.

5. The vascular device of claim 3, wherein loops of first and second retention portions are substantially perpendicular to a longitudinal axis of the elongated member.

6. The vascular device of claim 1, wherein the first retention portion includes first and second looped portions.

7. The vascular device of claim 1, wherein the second retention portion includes first and second looped portions.

8. The vascular device of claim 1, further comprising a collar mounted on the intermediate looped portion.

9. The vascular device of claim 1, wherein the second member is slidable with respect to the intermediate looped portion.

10. The vascular device of claim 9, wherein the first member is fixedly attached to the intermediate looped portion.

11. The vascular device of claim 1, further comprising a first collar mounted on the intermediate looped portion, the second member slidable within the first collar.

12. The vascular device of claim 1, wherein the elongated member, the intermediate looped portion, the first retention portion and the second retention portion are formed from a single wire.

13. The vascular device of claim 1, wherein the valve has a substantially conical configuration.

14. The vascular device of claim 1, further comprising retrieval structure at the upstream and downstream portions of the elongated member for retrieval of the device.

15. The vascular device of claim 1, wherein the first and second retention portions extend radially on one side of the elongated member.

16. A method for treating venous valve insufficiency comprising:
   providing a vascular device including an elongated portion and downstream, upstream and intermediate looped portions extending radially from the elongated portion, and a valve attached to the intermediate looped portion;
   inserting into a target vessel a delivery device and the vascular device in an insertion position within the delivery device, wherein in the insertion position the downstream, upstream and intermediate looped portions have a reduced transverse dimension; and
   exposing the vascular device from the delivery device, wherein exposing the vascular device enables the downstream, upstream and intermediate looped portions to move to the expanded position, the intermediate looped portion engaging an internal wall of the vessel and automatically adjusting to a diameter of the vessel;

wherein a diameter of the valve is adjusted by a radial support attached to the valve and slidably connected to the intermediate looped portion.

17. A vascular device for treating vein valve insufficiency comprising:

an elongated member having a first upstream portion and a second downstream portion;

a first retention portion at the first upstream portion, the first retention portion movable from a first elongated insertion position to an expanded position;

a second retention portion at the second downstream portion, the second retention portion movable from a first elongated insertion position to an expanded position:

an intermediate looped portion positioned between the first upstream portion and the second downstream portion;

a valve supported by the intermediate looped portion and movable between an open position to allow blood flow therethrough and a closed position to inhibit blood flow therethrough;

a retrieval structure at the upstream and downstream portions of the elongated member for retrieval of the device; and wherein the intermediate looped portion is composed of a material enabling the intermediate looped portion to be adjustable to loops of different diameters dependent on an inner diameter of the vessel wall;

wherein a collar is mounted to the intermediate looped portion and a radial support is slidable within the collar.

18. The vascular device of claim 1, wherein the intermediate looped portion is composed of a shape memory material.

* * * * *